United States Patent [19]

Fischer et al.

[11] 4,401,518

[45] Aug. 30, 1983

[54] METHOD OF MEASURING THICKNESS OF A TIN LAYER AND THICKNESS MEASURING DEVICE THEREFOR

[76] Inventors: Helmut Fischer, Bergwaldstrasse 28, 7261 Gechingen; Willi Steegmuller, Kornstrasse 18, 7407 Rottenberg/Ergenzingen, both of Fed. Rep. of Germany

[21] Appl. No.: 231,689

[22] Filed: Feb. 5, 1981

[51] Int. Cl.³ .................. G01N 27/26; G01N 27/28
[52] U.S. Cl. ................................. 204/1 T; 204/400
[58] Field of Search .............. 204/1 T, 195 R, 224 R

[56] References Cited

U.S. PATENT DOCUMENTS 2,457,234  12/1948  Herbert et al. ............... 204/195 R

FOREIGN PATENT DOCUMENTS 2658357  6/1978  Fed. Rep. of Germany ... 204/195 R
1360811  4/1964  France ........................... 204/224 R

OTHER PUBLICATIONS

Stanley Anderson et al., The Electrochemical Society, Preprint 78-3, pp. 37-46, (1940).

*Primary Examiner*—G. L. Kaplan

[57] ABSTRACT

An electrolyte chamber has an opening on the side facing the foil to be measured for letting the electrolyte through to the foil, a hollow cathode in the chamber, a supply line connected to the chamber through the hollow cathode for supplying the electrolyte to the chamber, and a negative pressure flow-off line connected to the chamber located at a distance from the mouth of the supply line. A negative pressure generator is connected to the flow-off line through a separator vessel which has a level switch which shuts off the generator when the electrolyte reaches a predetermined level. The supply line is connected to a supply vessel containing the electrolyte and runs continuously into the liquid volume in the vessel. The vessel has a connection to the atmosphere.

10 Claims, 6 Drawing Figures

METHOD OF MEASURING THICKNESS OF A TIN LAYER AND THICKNESS MEASURING DEVICE THEREFOR

The invention relates to an electrolyte chamber having an opening on the side facing the layer to be measured, for letting electrolyte through to the foil. Such a device is described in German Patent Disclosure 26 58 357. It concerns a special device inasmuch as it makes it possible to measure the thickness of a deposited layer, preferably a tin layer, on both sides of the foil. In addition, a relatively large volume of several tens to several hundred cubic centimeters is available to each hemisphere.

BACKGROUND OF THE INVENTION

For some time the Applicant has marketed devices, in quantities distributed on a larger scale, where the electrolyte chamber has several volume-cubic centimeters of which only a few, e.g. 1 to 3 cubic centimeters, are used for filling. This small volume electrolyte chamber has an opening on the bottom with which the chamber is placed on a sample. The cathode is provided coaxially in the form of a hollow rod and, in order to maintain an approximately uniform electrolyte concentration, the device is equipped with a motor generating pulsed air pressure variations which are transmitted via the cathode to the volume so that the electrolyte rises and drops in synchronism with this impulse. For large volume electrolyte chambers such movement generation is not necessary since the volume is sufficiently large and the electrolyte is capable of circulating. Effective electrolyte flow does not exist in small volume electrolyte chambers, which always have an opening of the order of magnitude of several square millimeters.

For measurements of this type according to FIG. 1 of our above specified publication, the voltage increase must be as steep as possible also in those cases where an alloy layer is present between the layer and the substrate material, which is formed during thermal treatment. In one case Sn is the layer and iron is the substrate material. The alloy layer located between them is FeSn$_2$.

The steepest slope is obtained when the alloy layer is completely uniformly removed, so that its thickness decreases uniformly everywhere, primarily in the final measuring phase.

OBJECT AND STATEMENT OF INVENTION

The object of the invention is to provide a thickness measuring device for thermally or galvanically deposited metal layers, where the slope of the voltage jump varies intermittently.

According to the invention this problem is solved with a device having:

(a) a negative-pressure flow-off line, connected to the electrolyte chamber, located at a distance from the mouth of the supply line in the electrolyte chamber, (b) a negative-pressure generator connected to the flow-off line, and (c) a supply vessel for electrolyte, having a connection with the atmosphere, the supply line being negative-pressure-proof and running continuously into the fluid volume of electrolyte in the supply vessel.

Also, the object of the invention is achieved by the method comprising:

arranging an electrolyte chamber, having an internal cathode, against the layer to be measured, with an opening for letting electrolyte through to the foil, supplying electrolyte to the electrolyte chamber from a supply vessel having a connection to the atmosphere, and applying a negative-pressure to the electrolyte in the electrolyte chamber through a flow-off line connected to the electrolyte chamber.

Good results are obtained as soon as the negative-pressure reaches only 100 mm water column. The effect of a very rapid pressure increase is further increased when a lower negative-pressure is chosen. The side effect is that it can now be seen whether or not the system is sealed. Gas bubbles are visible on leaky spots, which are produced by air sucked in from the outside.

The invention obviously makes it possible to remove the metal layer and the diffusion layer under it in a completely uniform manner without any island formation, so that for mechanical indicators the slope of the voltage jump is determined almost only by their inertia.

In addition, the invention has the following advantageous characteristics:

A separator vessel for the electrolyte is provided in front of the negative-pressure generator which is negative-pressure-proof. This characteristic provides that the negative-pressure generator must generate the negative-pressure of air, this negative-pressure indirectly resulting in an negative-pressure in the electrolyte. The negative-pressure per se can be generated with a liquid pump, which is more expensive than an air pump and must be of a special design on account of the electrolyte properties.

The separator vessel connected between the flow-off line and the negative-pressure generator, is equipped with a level switch, which switches off the energy supply to the negative-pressure generator. These characteristics reliably prevent electrolyte fluid from penetrating into the negative-pressure generator, which would eventually impair the air negative-pressure generator.

The electrolyte chamber is a thimble-type-electrolyte chamber i.e. having generally the shape and size of a sewing thimble in which the cathode is hollow and is the beginning of the supply line. This characteristic allows the fresh electrolyte flow to continuously reach the area where the electrolyte is most required. The cathodes are arranged coaxially with respect to the opening of the electrolyte chamber, so that a completely symmetrical flow pattern is obtained.

The opening in small electrolyte chambers is small and the opening accommodates a certain electrolyte volume which also is small. If the electrolyte flow would be pumped back and forth, then zero flow times would occur between every change of direction. In addition, at least a part of the electrolyte volume would be washed back to its old site. This is prevented by the characteristics in which the electrolyte chamber is a small-volume electrolyte chamber in which an electrolyte flow is provided in the supply line and the electrolyte chamber is negative-pressure-proof.

The electrolyte chamber is a large-volume electrolyte chamber in which electrolyte flow is not provided in the supply line. This characteristic results in a reduction of cost in those cases where an electrolyte flow is found earlier and the danger that the electrolyte is depleted is slight.

The under-pressure is larger than the flow-off tendency of the electrolyte from the opening. This characteristic makes it possible to simply change to the small volume electrolyte chamber, in particular the thimble-type electrolyte chamber, and to place it on a new measuring point. Heretofore it has been necessary to remove the electrolyte from the thimble with a pipette. This is only partially drip-proof, so that the samples to be measured, the measuring device, the hands of the attendants or their clothing are damaged. In addition, according to the state of the art, the pipette fluid had to be emptied into a storage container for used electrolyte. Then the thimble had to be lowered onto the new measuring point in such a way that its opening was tightly mounted. After that the thimble cover with electrolyte was removed and fresh electrolyte fluid was pipetted into it. The measurement could be started after the cathode and cover were again in operating position. All of these circumstances are avoided by this characteristic.

Several feeding supply vessels are used in which the supply lines thereof extend to the front of the electrolyte chamber. A first multi-position stopcock is used, into which the supply lines run and from which a short common line extends to the electrolyte chamber. A second multi-position stopcock is also used. A short common line extends downstream from the electrolyte chamber to the second multi-position stopcock and the flow-off lines extend from the outlets of the second multi-position stopcock. Each flow-off line leads to a separator vessel. These characteristics make it possible for the work to be carried out in a rapid time sequence with different electrolytes, employing only a short rinsing time with distilled water.

A common resetting device is used with which the two multi-position stopcocks can be reset. This characteristic makes it possible to reverse the two stopcocks with the same grip.

DESCRIPTION OF THE DRAWINGS

The invention will now be described on the basis of preferred exemplified embodiments in the drawing as follows.

DETAILED DESCRIPTION

Figure 1:
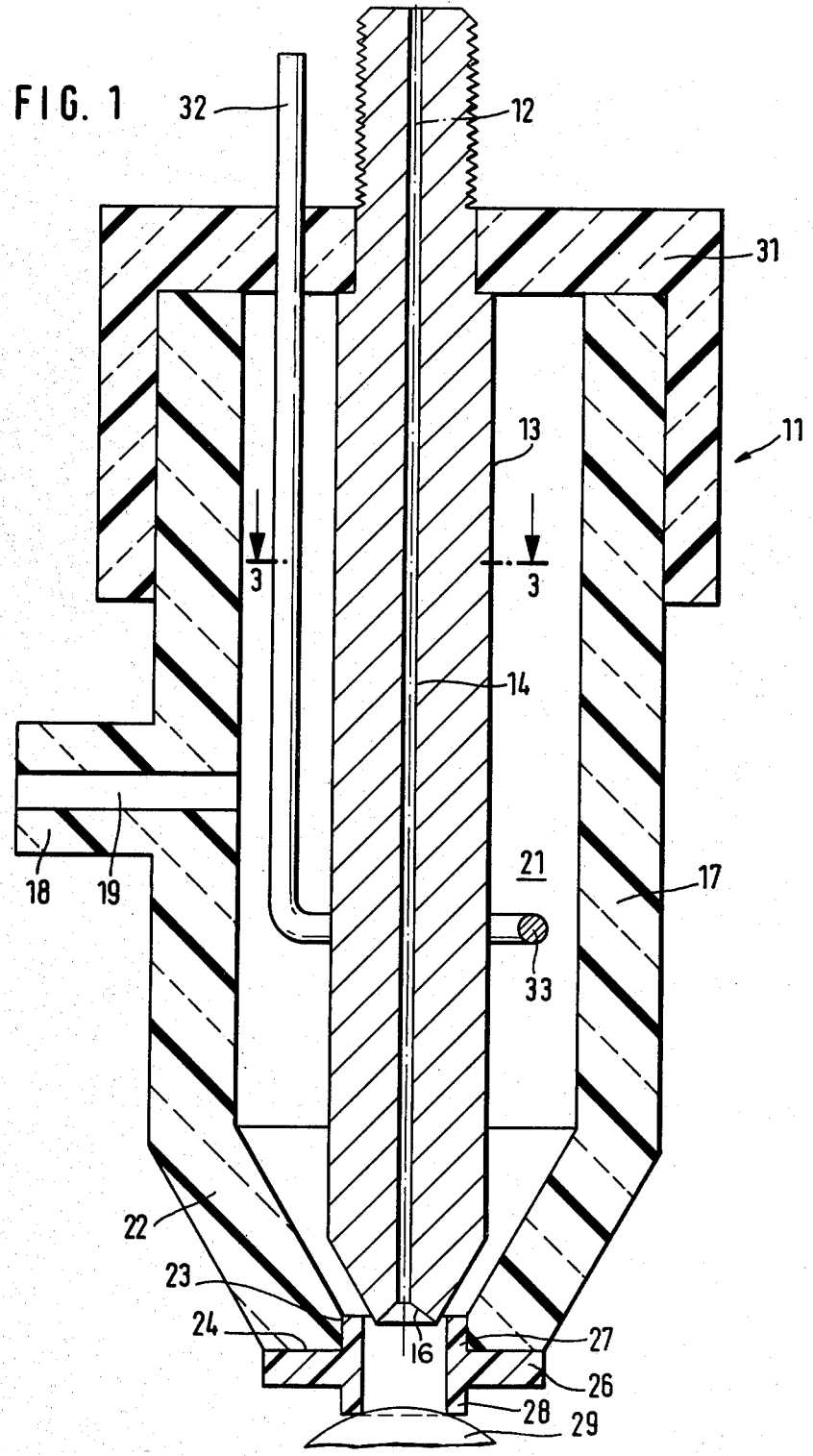
FIG. 1 shows a cross-section through a thimble measuring cell.

According to FIG. 1, chamber 11 is shaped like a thimble. It is largely coaxial with respect to longitudinal axis 12. A cathode in the shape of a small metal tube 13 extends coaxially to it from top to bottom, the channel 14 of which opens on the bottom in a cone 16. Chamber 11 has a cylinder wall 17 coaxial to the longitudinal axis 12, which is equipped with a connecting socket 18 on the left, establishing via channel 19 the connection to interior space 21 of the chamber. On the bottom cylinder wall 17 goes over into a funnel wall 22 in one piece, which has coaxial mounting walls 23, 24 on the bottom. The mounting walls grasp a flange attachment 26 about 4 mm in diameter. Cone 16 extends into the coaxial cylinder 27 of the flange attachment 26. Cylinder 27 extends downward over the flange extending out to the side and forms there a circular sealing lip 28, which sits on a curved measuring object 29. Sealing lip 28 encompasses an exactly defined area.

On the top the cylinder wall 17 is closed hermetically by a cover 31, through which tube 13 passes in airtight fashion. Further, connecting wire 32 passes hermetically through cover 31, extending downward in parallel to longitudinal axis 12 and forming an auxiliary electrode 33 on the bottom in the area between connecting socket 18 and funnel wall 22. It consists of a wire ring coaxially bent from connecting wire 32. The volume of interior space 21 amounts to 4 cubic centimeters. It is of the same size as that of the prior art thimble chambers. However, it could easily be half the size or it could have a quarter of the volume. In operation, chamber 11 is negative-pressure-proof.

Figure 2:
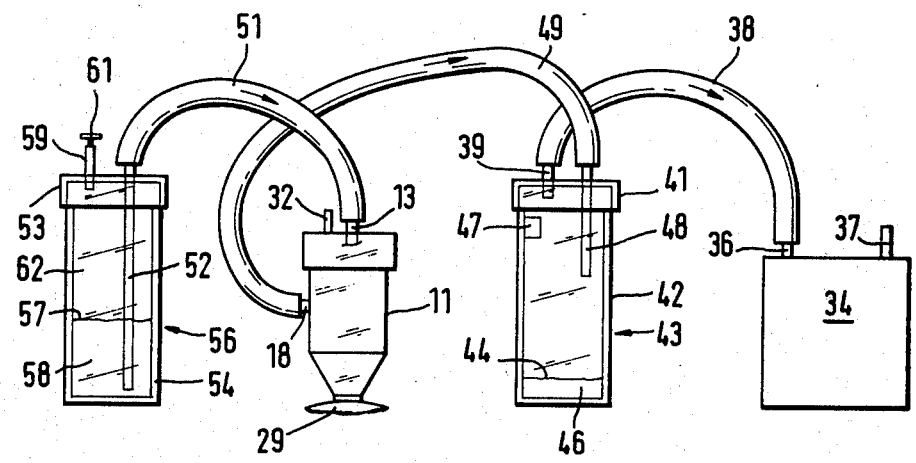
FIG. 2 shows a schematic circuit diagram of the components of the invention.
Figure 3:
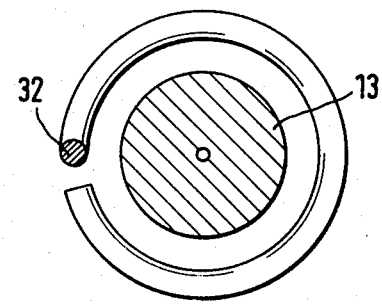
FIG. 3 shows a section along line 3—3 in FIG. 1.

FIG. 2 shows the complete layout of this exemplified embodiment in accordance with the invention. On the right there is an electrically driven negative-pressure generator 34, which is designed as an electrical oscillating armature pump. It sucks up air over a nozzle 36 and blows out air over a nozzle 37. The right end of a suction hose 38 is pushed on nozzle 36 in negative-pressure-proof fashion, the left end of which is pushed on a nozzle 39. This nozzle 39 passes hermetically through cover 41 of cup 42 of separator 43. Cup 42 preferably consists of glass and, therefore, is insensitive to the electrolyte and it can be seen where level 44 of separated electrolyte 46 is located. Nozzle 39 extends only slightly into cup 42. A schematically indicated float switch 47 is located under its lower end, which switches off the motor of negative-pressure generator 34 as soon as level 44 has reached float switch 47. In this way suction hose 38 always contains only air and the negative-pressure generator does not need to be designed in an electrolyte-proof manner.

A further nozzle 48 passes through cover 41 in airtight fashion and also extends into cup 42. The right end of a section hose 49 is pushed, in negative-pressure-proof fashion, on the part of nozzle 48 that extends to the outside. Suction hose 49 carries electrolyte fluid, which drips from the bottom end of nozzle 48 into cup 42.

The left (or upstream) end of section hose 49 is pushed in negative-pressure-proof fashion on connecting socket 18 of chamber 11. The upstream end of a suction hose 51 is pushed in negative-pressure-proof fashion on the outwardly extending part of tube 13, which, in addition, is electrically connected as cathode. Suction hose 51 carries electrolyte fluid. The downstream end of suction hose 51 is pushed in negative-pressure-proof fashion on the protruding end of a suction tube 52, which passes through a cover 53 in negative-pressure-proof fashion. Cover 53 is inserted in negative-pressure-proof fashion on cup 54 of a glass supply vessel 56. Suction tube 52 has its bottom end near the bottom of cup 54. It is filled with electrolyte fluid 58 up to level 57. Nozzle 59 passes through cover 53 in air-tight fashion and on its outer end it is equipped with an adjustable air resistor 61, which can be designed in the form of a stopcock, a stopper or similar device. If air resistor 61 is completely open, then ambient air pressure prevails in space 62 and the flow velocity of the electrolyte in the direction of the arrows in suction hoses 38, 49, 51 is then at the highest value. The further the air resistor 61 is closed, the slower the flow and the slower the drip of the electrolyte from nozzle 48.

If electrolyte 58 has been suctioned out, then electrolyte 46 is in cup 42. Cup 42 is then screwed off, as is cup 54, the two are changed and the measuring is continued. Measuring can be continued for a long time when cups 42, 54 are filled with one to several liters electrolyte.

Float switch 47 can be eliminated when cup 54 is only filled with so much electrolyte that level 44 is never at the height of the lower end of nozzle 39.

Figure 4:
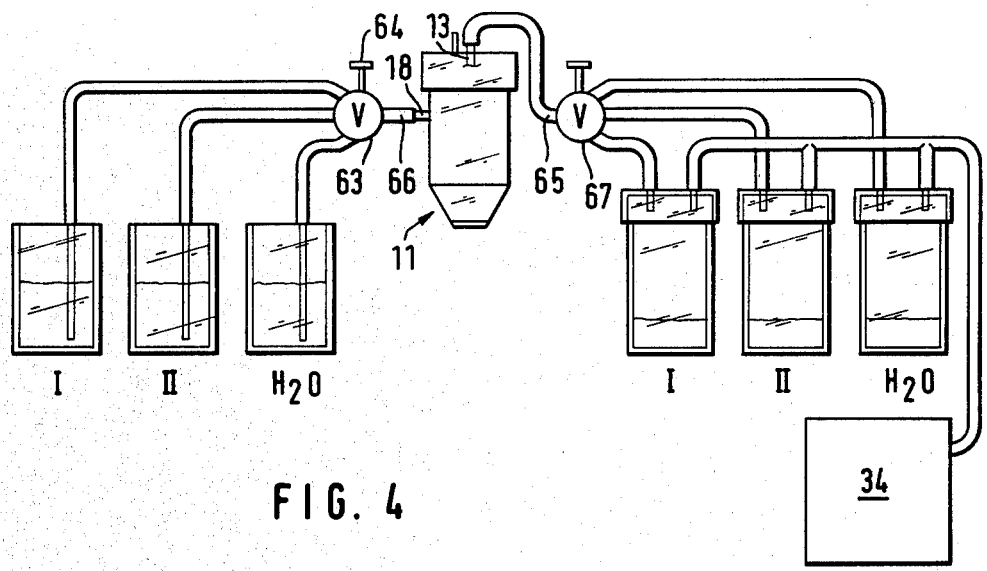
FIG. 4 shows a schematic of the operation of a thimble chamber with two different electrolytes and rinsing liquid.

FIG. 4 shows a scheme which is expanded compared to FIG. 2 since it operates with two electrolytes I and II in two cups and distilled water in a third cup. In this case the cups can also be provided with covers. For the sake of simplicity they are shown open. These three cups are each connected, via suction tubes and suction hoses, to three inlets of a three-way stopcock 63 which over its setting element 64 can connect one of the three inlets to its outlet 66 connected to outlet nozzle 18. A further three-way stopcock 67 is connected by its inlet 65 to tube 13 and its three outlets are connected via suction tubes with the interior of separation vessels. The left separation vessel is provided for electrolyte I, the center separation vessel is provided for electrolyte II, and the right separation vessel is provided for the rinsing fluid distilled water.

The negative-pressure generator 34 is connected to the space, not filled with fluid, of the separator vessels. The separator vessels are negative-pressure-proof in the manner specified above.

Three-way stopcocks 63, 67 are connected to one another in such a way that they have a common setting element 64 so that during operation electrolyte I flows from the left cup into the left separator vessel and so on.

Figure 6:
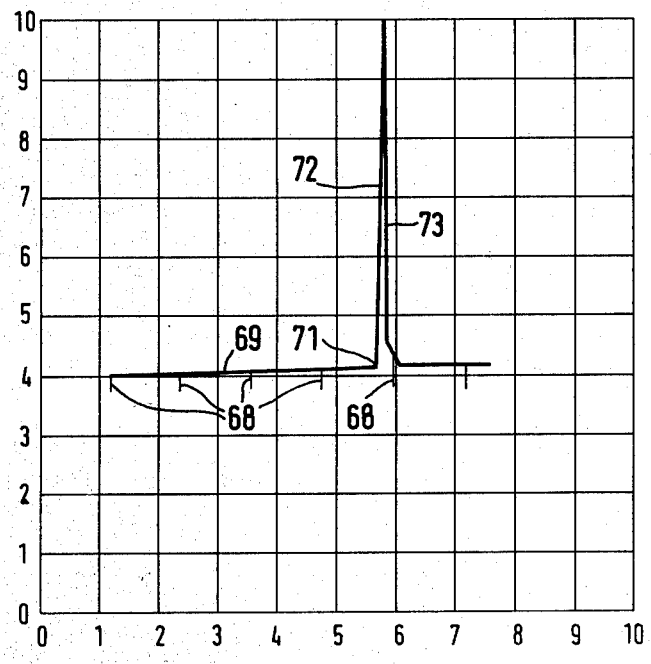
FIG. 6 shows a time/voltage plot of the detachment process.

If, in the exemplified embodiment according to FIG. 1 or 2, a voltage is applied to connecting wire 32 and the measuring object 29, the negative-pressure generator 34 is switched on, and the current between connecting wire 32 and the measuring object 29 is measured, then the voltage characteristic in FIG. 6 is obtained. Dashes 68 indicate the time progressing to the right. It can be seen that the curve branch 69 has a very slight slope. Kink 71 is followed by an almost vertical curve branch 72, the slope of which in FIG. 6 is actually caused more by the mechanical sluggishness of the recorder and which represents the voltage measured between the anode and the auxiliary cathode, whereas the total height of FIG. 6 amounts to 5 volts. The descending curve branch 73 is caused by switching off the current and is not indicative of anything. According to FIG. 6, it is clear that the separation process was completed in exactly 7.7 seconds.

Figure 5:
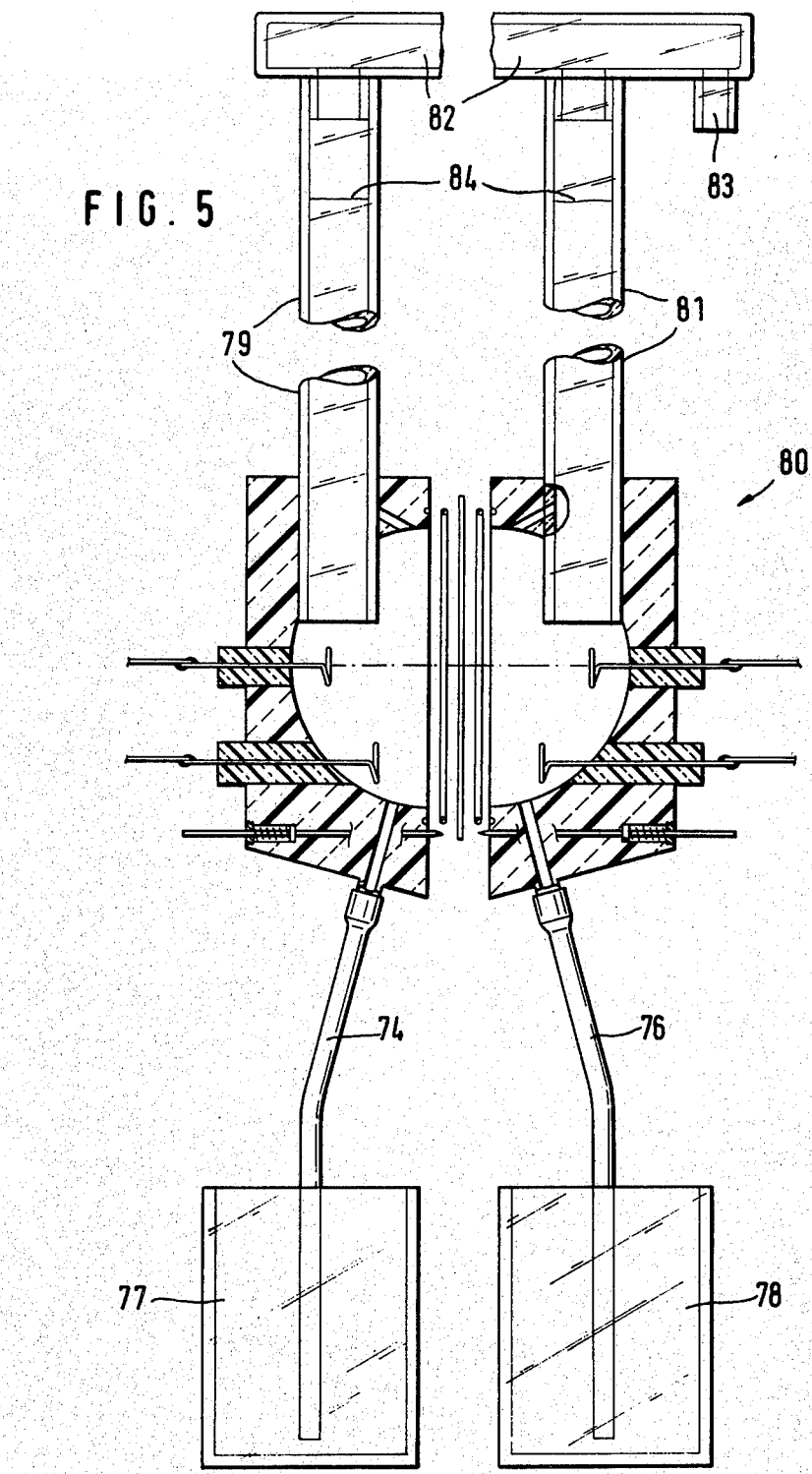
FIG. 5 shows the invention applied to a large volume electrolyte chamber, where the electrolyte chamber is shown at a 1:1 scale.

FIG. 5 shows the otherwise unmodified device of FIG. 2 which has been adapted to the invention in FIG. 5 from German Patent Disclosure 26 58 357. Since the Patent Disclosure gives a detailed description of the modus operandi of this device, the average technician is familiar with the functioning so that only the differences need be described:

Without the hose clamps required in the prior art case, the negative-pressure hoses 74, 76 are arranged here hanging down and lead into vessels 77, 78 which contain the same electrolyte. Therefore, an electrical separation through hose clamps is avoided. The hoses used previously for collecting gas bubbles are here run upwards as uptake hoses 79, 81 for several decimeters. They are located in a negative-pressure-proof fashion in the connecting yoke 82. On the top uptake hoses 79, 81 are mounted in negative-pressure-proof fashion in connecting yoke 82 which itself is negative-pressure-proof but is hollow. It is equipped with a suction nozzle 83, which is run to a suction hose the same as that designated 49 in FIG. 2. From there on the device is completely identical with the one shown in FIG. 2. As a result of the negative-pressure of the negative-pressure generator, the electrolyte in the device according to FIG. 5 rises in negative-pressure hoses 74, 76 to equal height up to level 84. If the uptake hoses 79, 81 consist of a transparent material, it is possible to control and/or prevent the electrolyte from reaching the connecting yoke 82. However, if suction nozzle 83 is connected to a separator vessel, identical with separator vessel 43 in FIG. 2 with floater switch, then it can be avoided that the negative-pressure generator receives electrolyte. If the separator vessel for the exemplified embodiment in FIG. 5 is arranged higher than vessels 77, 78 and the nozzle, corresponding to nozzle 48, is extended to the bottom of a cup corresponding to cup 42, then, after the negative-pressure generator is switched off through the floater switch, the electrolyte flows back completely on the basis of the fluid level principle.

Chamber 80 is naturally also emptied when the negative-pressure generator is switched off and level 84 drops to the fluid level in vessels 77, 78.

For the electrolytic thickness measuring technique the layers can be applied either galvanically or applied in a melt bath. A frequent application is galvanically applied tin on food cans or pyrolytically tin-plated can foils. This is also valid for zinc or fired-zinc plating, where the SENDZIMIR zinc-plating is the most frequently employed. However, it may also be necessary to measure chromium layers on chromium-plated objects, or brass layers on brass-plated steel objects. Another application is a brass base layer or TOMBACK plated with a tin/lead alloy.

The invention entails a very unappreciable hydrogen formation in the anode so that the previously formed, numerous and, at times, very large hydrogen bubbles are avoided, which, as a result of their rising, caused a premature switching off of the measuring device and simulated an apparent voltage jump.

Despite the slight hydrogen formation, the invention allows working at a higher current density, so that the measuring time is reduced at a ratio of 1:3.

Since extremely small measuring cells can be produced for a flowing electrolyte, measurements can also be made on curved parts in hollow objects or in narrow crevices.

What is claimed is:

1. In a device for measuring the thickness of a metal deposition layer on a metal sheet having an electrolyte chamber which, on the side facing the metal sheet, has an opening for letting through electrolyte to the metal sheet,
   a cathode in the electrolyte chamber, and
   a supply line for the electrolyte, connected liquid-tight to the electrolyte chamber, the improvement comprising:
   (a) a sealing device at the chamber opening arranged to provide a negative pressure-proof seal between the opening and the layer on the metal sheet,
   (b) a negative pressure flow-off line, connected to the electrolyte chamber, located at a distance from the mouth of the supply line in the electrolyte chamber, (c) a negative pressure generator connected to the flow-off line, a supply vessel for electrolyte, having a connection with the atmosphere, and (e) the supply line being negative pressure-proof and running continuously into the fluid volume of electrolyte in the supply vessel.

2. Device according to claim 1 in which a separator vessel for the electrolyte is provided in front of the negative pressure generator which is negative pressure-proof.

3. Device according to claim 1, comprising a separator vessel connected between the flow-off line and the negative pressure generator, and equipped with a level switch, which switches off the energy supply to the negative pressure generator.

4. Device according to claim 1, wherein the electrolyte chamber is a thimble-shaped cup in which the cathode is hollow and is the beginning of the supply line.

5. Device according to claim 1, in which the electrolyte chamber has an internal chamber volume large enough to support the electrolyte measurement process in which electrolyte flow is not provided in the supply line.

6. Device according to claim 1, in which the electrolyte chamber has an internal chamber volume and an opening small enough to support the flow of electrolyte in the supply line and negative pressure at the opening, in which the electrolyte chamber is negative pressure-proof and an electrolyte flow is provided in the supply line.

7. Device according to claim 6, comprising means for setting the negative pressure larger than the flow-off tendency of the electrolyte from the opening.

8. Device according to one of the claims 1 or 6, comprising at least two supply vessels in which the supply lines thereof extend to the front of the electrolyte chamber, a first multi-position stopcock into which the supply lines run, from which a short common line extends to the electrolyte chamber, a second multi-position stopcock, a short common line extending downstream from the electrolyte chamber to the second multi-position stopcock, the flow-off lines extend from the outlets of the second multi-position stopcock, and a separator vessel to which each flow-off line leads.

9. Device according to claim 8, comprising a common resetting device with which the two multi-position stopcocks can be reset.

10. Method for measuring the thickness of a metal deposition layer on a metal sheet comprising arranging against the layer to be measured an electrolyte chamber, having an internal cathode with an opening for letting electrolyte through to the metal sheet, providing a negative pressure-proof seal between the opening and the layer, supplying electrolyte to the electrolyte chamber from a supply vessel having a connection to the atmosphere, and applying a negative pressure to the electrolyte chamber through a flow-off line connected to the electrolyte chamber.

* * * * *